United States Patent [19]
Bartley et al.

[11] Patent Number: 6,031,035
[45] Date of Patent: Feb. 29, 2000

[54] PROCESS FOR MAKING AND USING BISARYL DIPHOSPHATES

[75] Inventors: David W. Bartley, West Lafayette; Timothy J. Lawlor, Lafayette, both of Ind.

[73] Assignee: Great Lakes Chemical Corporation, West Lafayette, Ind.

[21] Appl. No.: 09/023,634

[22] Filed: Feb. 13, 1998

[51] Int. Cl.⁷ ..................................................... C08K 5/53
[52] U.S. Cl. ............................................................ 524/126
[58] Field of Search .............................................. 524/127

[56]  References Cited

U.S. PATENT DOCUMENTS

| | | |
|---|---|---|
| 2,520,090 | 8/1950 | Barrett . |
| 4,134,876 | 1/1979 | Horner et al. . |
| 4,267,127 | 5/1981 | Selbeck et al. .......................... 260/973 |
| 4,343,732 | 8/1982 | Zama et al. . |
| 4,933,386 | 6/1990 | Nitoh et al. . |
| 5,011,736 | 4/1991 | Abolins et al. . |
| 5,104,450 | 4/1992 | Sand et al. . |
| 5,135,973 | 8/1992 | Fukasawa et al. ......................... 524/94 |
| 5,204,394 | 4/1993 | Gosens et al. . |
| 5,281,741 | 1/1994 | Gunkel et al. . |
| 5,294,654 | 3/1994 | Hellstern-Burnell et al. . |
| 5,420,327 | 5/1995 | Bright et al. . |

FOREIGN PATENT DOCUMENTS

| | | |
|---|---|---|
| 0 129 824 A1 | 1/1985 | European Pat. Off. . |
| 0 129 825 A3 | 1/1985 | European Pat. Off. . |
| 0 509 506 A2 | 10/1992 | European Pat. Off. . |
| 0 657 498 A1 | 6/1995 | European Pat. Off. . |
| 0 672 717 A1 | 9/1995 | European Pat. Off. . |
| 0 690 063 A1 | 1/1996 | European Pat. Off. . |
| 2 043 083 | 10/1980 | United Kingdom . |
| 90/03417 | 4/1990 | WIPO . |
| 96/06885 | 3/1996 | WIPO . |
| 96/20263 | 4/1996 | WIPO . |
| 96/13508 | 5/1996 | WIPO . |
| 96/17887 | 6/1996 | WIPO . |

OTHER PUBLICATIONS

Abstract: Japan JP 09192506 Matsubara et al.
Abstract: Japan JP 09012587 A2 Matsubara et al.

*Primary Examiner*—Kriellion Sanders
*Attorney, Agent, or Firm*—Woodard, Emhardt, Naughton Moriarty & McNett

[57]  ABSTRACT

Flame retardancy is provided to polymer resins by adding to the resin a bisaryl diphosphate that has not been purified to remove catalyst or catalyst residue from the product. The bisaryl diphosphate may be prepared by a two-step process that starts with the semi-continuous addition of dry bisphenol A to a heated mixture of phosphorus oxychloride and MgCl, and concludes with the addition of dry phenol to the step one intermediate.

16 Claims, No Drawings

PROCESS FOR MAKING AND USING BISARYL DIPHOSPHATES

FIELD OF THE INVENTION

The present invention relates generally to the manufacture and use of bisaryl diphosphates, and more particularly to an improved process for making and using bisphenol A bis(diphenyl)-phosphate without purification.

BACKGROUND OF THE INVENTION

Bisaryl diphosphates such as bisphenol A bis(diphenyl)-phosphate can be effective flame retardants for polymer resins. For example, polyphenylene oxide/high-impact polystyrene ("PPO/HIPS") and polycarbonate/acrylonitrile-butediene-styrene ("PC/ABS") blends can be improved with bisaryl diphosphate flame retardants.

Because of their commercial utility, various processes for the manufacture of bisaryl diphosphates have been developed. For example, it is known that bisphenol A bis(diphenyl)-phosphate can be obtained by catalytically reacting a phosphorus oxyhalide with bisphenol A and then reacting the intermediate with phenol.

Prior art processes for making and using bisaryl diphosphates include one or more steps to remove the catalyst from the diphosphate. The most common method employed for catalyst removal has been by aqueous washing which leads to emulsions with the product. However, the residual water must generally be removed prior to use as a flame retardant.

Prior art processes for making and using bisaryl diphosphates also disclose that the triaryl phosphate content of the final products should be reduced. Accordingly, prior art processes typically employed a non-reactive solvent to reduce triaryl phosphates.

In view of the above it can be seen that a need exists for improved methods of flame retarding polymer resins with bisaryl diphosphate compounds. The present invention addresses that need.

SUMMARY OF THE INVENTION

Briefly describing one aspect of the present invention, there is provided a method of effectively and economically making flame retarded polymer resins by adding to the polymer resin a catalytically synthesized bisaryl diphosphate that has not been purified to remove catalyst from the product, so that the synthesized bisaryl diphosphate provided to the resin contains the catalyst (or the residue of the catalyst) used to make the bisaryl diphosphate.

In another aspect of the invention, the flame retarded polymer resins referred to above are made using a bisaryl diphosphate that is the product of a process in which a dihydric aromatic compound (such as bisphenol A) is semi-continuously added to a heated catalyst/phosphorus oxyhalide mixture (such as a mixture of phosphorus oxychloride and MgCl) over a period of 0.5 hours to 12.0 hours. The resulting intermediate is then reacted with an alcohol (such as phenol) to form the desired bisaryl diphosphate.

Other aspects of the invention provide flame retarded polymer resins using bisaryl diphosphates prepared using other process limitations. In one method the dihydric aromatic compound (e.g., bisphenol A) contains less than about 200 ppm water. In another method the alcohol (e.g., phenol) contains less than about 300 ppm water.

One object of the present invention is to provide improved methods of flame retarding polymer resins.

Another object of the present invention is to provide new polymer resins that have been flame retarded at a minimum cost.

Still another object of the present invention is to provide improved methods of manufacturing bisaryl diphosphate compounds for use as flame retardants in polymer resins.

Related objects and advantages of the present invention will be apparent from the following description.

DESCRIPTION OF THE PREFERRED EMBODIMENT

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

As noted above, one aspect of the present invention provides a method of making flame retarded polymer resins by blending a catalytically prepared bisaryl diphosphate into a polymer resin without removing the catalyst (or catalyst residue) from the bisaryl diphosphate. Surprisingly, polymer resins that have been flame retarded in this way possess characteristics that compare favorably with those of resins made with bisaryl diphosphates only after removing the catalyst from the bisaryl diphosphate. While the $MgCl_2$ catalyst residue was expected to cause problems with the hydrolytic stability of PC/ABS, formulated resin with both the bisaryl diphosphate and the catalyst left in were found to be stable.

As to the polymer resins that can be used in the present invention, the bisaryl diphosphate/catalyst mixture may be used as a flame retardant in a wide variety of polymer resins. Preferred polymer resins include polyphenylene oxide (PPO), high-impact polystyrene (HIPS), polycarbonate (PC), polyurethane (PU), polyvinyl chloride (PVC), acrylonitrile-butadiene-styrene (ABS), and polybutylene terephthalate (PBT), but a wide range of other polymer resins may also be used. Blends of these and other resins, such as polyphenylene oxide/high-impact polystyrene blends (PPO/HIPS) and polycarbonate/acrylonitrile-butediene-styrene blends (PC/ABS) may also advantageously be made and used. The flame retardant may be added in the range of 5–30%, preferably, 10–20%.

As to the bisaryl diphosphate/catalyst mixtures that are formulated into the polymer resins, in the preferred embodiments the bisaryl diphosphate is made by the two-step process illustrated below.

STEP 1

1. A phosphorus oxyhalide is reacted with a dihydric aromatic compound in the presence of a catalyst. The dihydric aromatic is preferably semi-continuously added to a heated mixture of phosphorus oxyhalide and catalyst over a period of time of 0.5 hours to 12 hours.

2. The reaction mixture is heated to reflux temperatures in order to evolve the hydrogen chloride by-product gas and convert the dihydric aromatic compound into the corresponding diphosphorotetrachloridate.

3. Unreacted phosphorous oxyhalide is removed by distilling under reduced pressure leaving the step 1 intermediate product.

STEP 2

1. The crude step 1 intermediate is reacted with an alcohol to form the desired flame-retardant product.
2. The reaction is heated to sufficient temperatures to convert the intermediate to product.
3. A subsurface nitrogen sparge is introduced to remove the by-product hydrogen chloride.
4. Excess alcohol is removed, by a reduced pressure strip if necessary. The product is used without any further purification.

As to the components used in the preferred embodiments, the phosphorus oxyhalide is of the formula $POX_3$, where X is bromine or chlorine. The most preferred phosphorus oxyhalide is phosphorus oxychloride, although phosphorus oxybromide can be used.

As to the dihydric aromatic compound used in the first step of the process, the preferred dihydric aromatic compounds include resorcinol, hydroquinone, bisphenol A, bisphenol S, bisphenol F, bisphenol methane, biphenols, and other substituted dihydric aromatic compounds. It is preferred that there be no more than one substituent ortho to each hydroxyl group on the dihydric aromatic compound. The most preferred dihydric aromatic compound is bisphenol A.

The ratio of the phosphorus oxyhalide to the dihydric compound is used to control the degree of polymerization in the final product. The preferred range is between one-half and five moles of phosphorus oxyhalide per mole of dihydric compound, although ratios outside this range may be used. The preferred range is merely representative of the process in its preferred embodiments.

The preferred catalysts promote the reaction and are soluble in the final product, although nonsoluble catalysts may be used. Many of the preferred catalysts are metal halide salts, but other types of compounds may be used to catalyze the reaction. Examples of preferred catalysts include aluminum chloride, magnesium chloride, calcium chloride, zinc chloride and titanium tetrachloride. The most preferred catalyst for use in this invention is magnesium chloride.

The amount of catalyst needed in the reaction is in the range of 0.01–2.0 wt. % based on the weight of dihydric aromatic compound. The most preferred range is 0.1–0.75 wt. %.

It is to be appreciated that heat is maintained on the reaction mixture until the dihydric aromatic compound has essentially been converted to the diphosphorotetrachloridate. This typically requires aging periods of 1–3 hours, depending on the particular dihydric compound chosen.

After the reaction is complete, the excess phosphorus oxyhalide may be removed by distillation. The distillation can be at reduced pressure, or at atmospheric pressure using elevated temperatures. Preferably, the phosphorus oxyhalide is removed with reduced pressure and elevated temperatures. Most preferably, the pressure is less than 20 torr and the temperature is between 150 and 180° C.

As to the alcohol used in the second step of the process, any alcohol may be used. Preferred alcohols are aromatic alcohols, although aliphatic alcohols may also be used —either alone or in combination with an aromatic alcohol. Preferred alcohols for use in the invention include ortho-cresol, meta-cresol, para-cresol, xylenols, phenol, halo-phenols and other substituted phenols. It is preferred that there be no more than one substituent ortho to each hydroxyl group on an aromatic alcohol. The more preferred alcohols are monohydric aromatic alcohols, most preferably phenol.

The ratio of alcohol to the diphosphorotetrachloridate intermediate is preferably at least 4 moles per mole based on reaction stoichiometry. Excesses of up to 10% are desired to increase the reaction rate and account for loss of the aromatic compound from the reactor. The preferred range is a 1–3% excess above stoichiometric requirements.

The alcohol is preferably added to the hot mixture from the first step in a semi-continuous fashion. The compound is added over the course of 0.5 to 12 hours. The reaction is conducted at a temperature such that the alcohol reacts with the step 1 intermediate. This temperature varies according to the substituents on both the alcohol and the dihydric aromatic compound from the first step. When the reaction components are bisphenol A, phosphorus oxychloride, and phenol, the preferred temperature range for the reaction of step 1 intermediate is 140–240° C. with the most preferable range being 150–180° C. The reaction temperature may be held constant after the addition of alcohol, or it may be increased to increase the reaction rate.

After essentially all of the step 1 intermediate has been converted to final product, the excess alcohol is distilled from the mixture, preferably under reduced pressure. The temperature, pressure and other reaction conditions for the distillation depend on the dihydric aromatic compound and alcohol being used, but when the reaction components are bisphenol A and phenol, the most preferred method is stripping in a wiped-film or falling-film evaporator using absolute pressures of less than 10 torr and temperatures of 165–220° C.

Alternatively, the present invention may be embodied in a process for the preparation of a bisaryl diphosphate as described below:

1. A phosphoryl compound of the formula $(RO)_2POX$, where X is bromine or chlorine and R is aromatic or aliphatic, is reacted with about a 0.5 molar quantity of a dihydric aromatic compound in the presence of a suitable catalyst.
2. The reaction mixture is heated to promote reaction and evolve the by-product hydrogen chloride gas. A nitrogen sparge may be introduced to the reaction to enhance evolution of hydrogen chloride.
3. The resulting product is distilled under reduced pressure to remove any volatile components. The product is used without any further purification.

In this alternative embodiment the aromatic/aliphatic group in the phosphoryl compound (the "R" group in the formula above) is derived from the reaction of an alcohol with a phosphorus oxyhalide. Suitable alcohols are identical to those listed above. The dihydric aromatic compound is also selected from those listed above.

Also in the alternative embodiment the dihydric aromatic compound is added to the hot phosphoryl compound in the temperature range of 100–240° C. Typical addition times range from 0.5 to 12 hours. When the reaction is complete, any volatile compounds are removed by distillation under reduced pressure in a wiped-film or falling-film evaporator in the temperature range of 165–220° C.

In the most preferred aspect of the present invention the bisaryl diphosphate used to flame retard the polymer resin is the product of a specific process for catalytically preparing bisaryl diphosphates. The process includes the semi-continuous addition of the dihydric aromatic compound to the phosphorus oxyhalide to reduce triaryl phosphate content, with semi-continuous addition being the addition of the dihydric aromatic compound to the heated catalyst/phosphorus oxyhalide mixture over a period of 0.5 hours to 12.0 hours. The resulting product is then reacted with an alcohol to form the desired bisaryl diphosphate.

The semi-continuous addition of the dihydric aromatic compound reduces the decomposition of this compound, particularly in the case of bisphenol A. The step 1 intermediate product therefore contains fewer decomposition products. Since these decomposition products are converted to triaryl phosphates in the second reaction, the use of the semi-continuous addition is effective to minimize the triaryl phosphate content in the final product. This is especially true when bisphenol A is used as the dihydric aromatic compound.

In another preferred aspect of the present invention the bisaryl diphosphate used to flame retard the polymer resin is the product of a process for catalytically preparing bisaryl diphosphates in which a dry dihydric aromatic compound (e.g., dry BPA) is used. Most preferably, the dihydric aromatic compound has a moisture content of <200ppm water. Using this technique it is possible to produce a supply of aryldiphosphate esters in which the monomer content is increased from about 60% to about 80%. This improves the physical properties of the formulated polymer, including melt flow, impact strength, and flame retardancy.

In another preferred aspect of the present invention the bisaryl diphosphate used to flame retard the polymer resin is the product of a process for catalytically preparing bisaryl diphosphates in which a dry alcohol (e.g., dry phenol) is used. Most preferably, the phenol has a moisture content of <300ppm. The effect of excess water is an increase in acidity of the final product which causes hydrolytic instability when formulated in PC/ABS. The effect of water in phenol is thus different than the effect of water in BPA.

In view of the above discussion of the importance of keeping water out of the BPA and phenol, it should also be recognized that it is important to also keep water out of the $POCl_3$. It is known to the art that $POCl_3$ reacts with water to form undesirable products, as shown below:

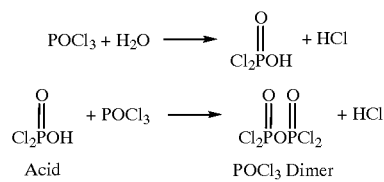

Water is therefore substantially eliminated from the $POCl_3$ in the most preferred embodiments. In certain preferred embodiments the $POCl_3$ is sufficiently water-free to assure that the dimer and acids levels in the $POCl_3$ are less than 0.2% by weight.

Reference will now be made to specific examples using the processes described above. It is to be understood that the examples are provided to more completely describe preferred embodiments, and that no limitation to the scope of the invention is intended thereby.

EXAMPLE 1
Bulk Addition of Bisphenol A

Step 1: Phosphorus oxychloride (3347.8g, 21.881 moles), magnesium chloride (2.85g, 0.030 moles), and bisphenol A (1425.4g, 6.24 moles) were charged into a flask equipped with a stirrer, heating mantle, temperature controller, and a reflux condenser vented to a caustic scrubber. The contents were heated to reflux for 6.75 hours and the reaction monitored for completion by liquid chromatography. After the reaction was complete, the flask was equipped for distillation and vacuum gradually applied until the pressure was less than 20 torr. The temperature of the flask contents was allowed to increase to 180° C. during this process. When the temperature reached 180° C., the distillation was stopped and the material was subsequently used in the second step.

Step 2: A portion of the step 1 intermediate (1095.8g) from the above reaction was charged into a flask equipped with a stirrer, heating mantle, temperature controller, and a reflux condenser vented to a caustic scrubber. The contents were heated to 180° C. and phenol (832.7g, 8.85 moles) was charged into an addition funnel. The phenol was added over the course of 3.5 hours. An hour after the addition was complete, a subsurface nitrogen sparge was introduced into the reactor. The reaction was monitored for completion by liquid chromatography. When the reaction was complete, vacuum was applied to the reactor for 1.0 hour to remove the bulk of the excess phenol. The product was analyzed by liquid chromatography and found to contain 96.1% by area bisaryl diphosphate (monomer and higher oligomers) and 4.5wt. % triphenyl phosphate.

EXAMPLE 2
Semi-Continuous Addition of Bisphenol A

Step 1: Phosphorus oxychloride (671.0g, 4.38 moles) and magnesium chloride (0.58g, 0.0061 moles) were charged into a flask equipped with a stirrer, heating mantle, temperature controller, and a reflux condenser vented to a water absorber. The flask contents were heated to 100° C. Bisphenol A (288.5g, 1.26 moles) was placed in a solids addition funnel and added to the flask over the course of 3 hours. At that time, the flask contents were heated to reflux and the reaction monitored for completion by liquid chromatography. After the reaction was complete, the flask was equipped for distillation and vacuum gradually applied until the pressure was less than 20 torr. The temperature of the flask contents was allowed to increase to 180° C. during this process. When the temperature reached 180° C., the distillation was stopped and the material was subsequently used in the second step.

Step 2: The contents of the flask from step 1 were heated to 165° C. Phenol (432.6g, 4.60 moles) was charged into an addition funnel wrapped with heat tape. The phenol was added to the reactor over the course of 2 hours. An hour after the addition was complete, a subsurface nitrogen sparge was introduced into the reactor. The reaction was monitored for completion by liquid chromatography. When the reaction was complete, vacuum was applied to the evaporator to remove the remaining phenol. The final product was analyzed by liquid chromatography and found to contain 98.7% by area bisaryl diphosphate (monomer and higher oligomers) and 0.76 wt. % triphenyl phosphate.

EXAMPLE 3
Use of dry BPA

Step 1: Phosphorus oxychloride and bisphenol A were reacted under magnesium chloride catalysis as described in Example 2, Step 1 (semi-continuous addition of BPA). The bisphenol A was analyzed for moisture prior to the reaction. Two different reactions were run using two different water levels in the bisphenol A. The product of both reactions was analyzed by liquid chromatography to determine the amount of monomeric and dimeric product. The table below shows that use of dry bisphenol A results in a step 1 intermediate product that has a higher content of the monomeric product relative to the dimeric product.

| Water in Bisphenol A | Area % Monomeric Product | Area % Dimeric Product | Normalized Area % Monomeric Product |
| --- | --- | --- | --- |
| 149 ppm | 74.8 | 17.1 | 81.4 |
| 500 ppm | 67.0 | 22.9 | 74.6 |

EXAMPLE 4
Use of Dry Phenol

Step 1: Two reactions were run to generate step 1 intermediate product as described in Example 2, Step 1 (semi-continuous addition of BPA). In both cases, bisphenol A with a moisture content of <200 ppm water was used. Normalized area % monomer content of the final product was >81%.

Step 2: The material from each of the step 1 reactions was reacted with phenol as described in Example 2, Step 2. The two reactions used phenol which had two different levels of moisture. The product was analyzed by liquid chromatography for the monomeric and dimeric content and analyzed by titration for acidity. The data in the table below show that the increased moisture in the phenol had no impact on the normalized monomer content in the final product. However, the acidity of the final product was affected.

| Water in Phenol | Normalized Area % Monomeric Product | Acid Value of Product (mg KOH/g) |
| --- | --- | --- |
| 222 ppm | 81.0 | 0.041 |
| 400 ppm | 81.0 | 0.248 |

EXAMPLE 5

It can also be seen that use of dry phenol (<300 ppm water) and use of dry BPA (<200 ppm water) results in a flame retarded polycarbonate which is hydrolytically more stable than that achieved using wet BPA or phenol. Polymer resin bars were compounded and molded from PC/ABS with bisphenol A bis(diphenyl)phosphate as described in Example 6. The formulated bars were subjected to accelerated test conditions (100° C. and 100% relative humidity) to determine hydrolytic stability. The molecular weight of the polycarbonate portion of the resin was monitored by gel permeation chromatography over time. The increased hydrolytic stability is indicated by the lower loss of molecular weight over time.

MOLECULAR WEIGHT OF POLYCARBONATE OVER TIME

| Time (hr.) | Dry BPA and Dry Phenol | Dry BPA Wet Phenol | Wet BPA and Dry Phenol |
| --- | --- | --- | --- |
| 0 | 46,800 | 44,274 | 43,049 |
| 9 | 44,678 | 44,513 | 40,166 |
| 15 | 45,730 | 38,205 | 37,630 |
| 24 | 42,304 | 33,293 | 33,554 |

EXAMPLE 6
Compounding Bisaryl Diphosphates Into Polymer Resins

The bisphenol A bis(diphenyl) phosphate produced in the above examples is compounded into various polymer resins using a Berstorff 25 mm twin screw extruder equipped with a 4 inch wide, variable speed, DC drive belt feeder. The twin screw extruder settings are tabulated below.

| | |
| --- | --- |
| Barrel 2 Temperature (° C.) | 240–260 |
| Barrel 3 Temperature (° C.) | 240–260 |
| Barrel 4 Temperature (° C.) | 240–260 |
| Barrel 5 Temperature (° C.) | 240–260 |
| Barrel 6 Temperature (° C.) | 240–260 |
| Barrel 7 Temperature (° C.) | 240–260 |
| Die Temperature (° C.) | 240–260 |
| Melt Temperature (° C.) | 240–270 |
| Melt Pressure (psi) | 240–560 |
| Torque (kilowats) | 0.17–0.25 |
| Extruder Speed (rpm) | 18–200 |

The bisphenol A bis(diphenyl) phosphate is heated in a 4-liter stainless steel resin kettle to approximately 80° C. While the bisphenol A bis(diphenyl) phosphate is heating, the belt feeder containing the polymer resin is calibrated to deliver the required feed rate into the throat of the extruder. Once the bisphenol A bis(diphenyl) phosphate has reached temperature, the heated Zenith pump is calibrated to deliver the desired feed rate of bisphenol A bis(diphenyl) phosphate into the third barrel of the twin screw extruder. The pumping system is then connected to the extruder by attaching the feedlines into the injection port located at the third barrel.

After the feed rates have been set, the polymer resin is fed into the twin screw extruder at the throat. The resin is allowed to pass through the extruder for several minutes before the bisphenol A bis(diphenyl) phosphate is added in order to ensure that any residual clean out material is purged from the extruder. After the purging step is complete, the pumping system is started and bisphenol A bis(diphenyl) phosphate is injected into the extruder through the feedlines and the injection port.

The melt pressure, measured at the interface between the seventh barrel and the die, is used as an indication that the bisphenol A bis(diphenyl) phosphate is being incorporated into the polymer resin. The base polymer resin generally has a melt pressure reading 100–200 psi greater than the bisphenol A bis(diphenyl) phosphate formulated polymer resin. Once the bisphenol A bis(diphenyl) phosphate is incorporated into the polymer resin, the melt pressure drops 100–200 psi due to bisphenol A bis(diphenyl) phosphate's ability to improve the flow properties of the polymer resin.

Once the bisphenol A bis(diphenyl) phosphate has been incorporated into the polymer resin, the material passes through the extruder die and strands through a water bath used for cooling. The cooled strands of formulated polymer resin are pellitized and used for molding flammability and physical test bars.

The same procedure is used for each individual polymer resin system. The main difference is in the amount of bisphenol A bis(diphenyl) phosphate added to the individual polymer resin systems. Representative examples are below. These formulations were all tested by the standard UL 94 procedure and found to be less flammable than the base resin.

1. PPO/HIPS: 20% bisphenol A bis(diphenyl) phosphate & 80% PPO/HIPS
2. PC/ABS: 11% bisphenol A bis(diphenyl) phosphate & 89% PC/ABS
3. PBT: 10% bisphenol A bis(diphenyl) phosphate & 90% PBT.

While the invention has been illustrated and described in detail in the foregoing description, the same is to be construed as illustrative and not restrictive in character, it being understood that only the preferred embodiment has been shown and described and that all changes and modifications that come within the spirit of the invention are desired to be protected.

What is claimed is:

1. A flame retarded polymer resin comprising a polymer resin, a catalytically prepared bisaryl diphosphate, and at least 10% (weight %) of the catalyst residue from the catalytic preparation.

2. The flame retarded polymer resin of claim 1 wherein said catalytically prepared bisaryl diphosphate is a catalytically prepared bisphenol A bis(diphenyl)phosphate.

3. The flame retarded polymer resins of claim 1 wherein said bisaryl diphosphate is a product obtained by a process that includes semi-continuously adding a dihydric aromatic compound to a heated mixture of phosphorus oxyhalide and a catalyst; wherein said semi-continuous addition takes place over a period of about 0.5 hours to about 12.0 hours.

4. The flame retarded polymer resins of claim 3 wherein the dihydric aromatic compound is bisphenol A.

5. The flame retarded polymer resins of claim 1 wherein the bisaryl diphosphate product is obtained by a process that includes:
   (a) reacting a dihydric aromatic compound with a catalyst/phosphorus oxyhalide mixture to produce a diphosphorotetrahalide intermediate, wherein said dihydric aromatic compound contains less than about 200 ppm water; and
   (b) reacting said diphosphoroetrahalide intermediate with an alcohol to form the desired bisaryl diphosphate.

6. The flame retarded polymer resin of claim 5 wherein said resin is a blend of a polymer resin and the bisaryl diphosphate product that is obtained by a process that includes:
   (a) reacting bisphenol A with a catalyst/phosphorus oxyhalide mixture to produce a diphosphorotetrahalide intermediate, wherein said bisphenol A contains less than about 200 ppm water; and
   (b) reacting said diphosphorotetrahalide intermediate with phenol to form bisphenol A bis(diphenyl)phosphate.

7. The flame retarded polymer resins of claim 1 wherein the bisaryl diphosphate product is obtained by a process that includes:
   (a) reacting a dihydric aromatic compound with a catalyst/phosphorus oxyhalide mixture to produce a diphosphorotetrahalide intermediate; and
   (b) reacting said diphosphorotetrahalide intermediate with an alcohol to form the desired bisaryl diphosphate, wherein said alcohol contains less than about 300 ppm water.

8. The flame retarded polymer resins of claim 7 wherein said resins comprise a polymer resin and the bisaryl diphosphate product that is obtained by a process that includes:
   (a) reacting bisphenol A with a catalyst/phosphorus oxyhalide mixture to produce a diphosphorotetrahalide intermediate; and
   (b) reacting said diphosphorotetrahalide intermediate with phenol to form bisphenol A bis(diphenyl)phosphate, wherein said phenol contains less than about 300 ppm water.

9. A method of making flame retarded polymer resins, comprising blending a catalytically prepared bisaryl diphosphate into a polymer resin without removing the catalyst residue from the bisaryl diphosphate.

10. The method of claim 9 wherein said blending step comprises blending a catalytically prepared bisphenol A bis(diphenyl)phosphate into a polymer resin before removing substantial amounts of catalyst residue from the bisphenol A bis(diphenyl)phosphate.

11. The method of claim 9 wherein said bisaryl diphosphate is prepared by a process that includes semi-continuously adding a dihydric aromatic compound to a heated mixture of phosphorus oxyhalide and a catalyst; wherein said semi-continuous addition takes place over a period of about 0.5 hours to about 12.0 hours.

12. The method of claim 11 wherein said dihydric aromatic compound is bisphenol A.

13. The method of claim 9 wherein said bisaryl diphosphate is prepared by a process that includes:
   (a) reacting a dihydric aromatic compound with a catalyst/phosphorus oxyhalide mixture to produce a diphosphorotetrahalide intermediate, wherein said dihydric aromatic compound contains less than about 200 ppm water; and
   (b) reacting said diphosphorotetrahalide intermediate with an alcohol to form the desired bisaryl diphosphate.

14. The method of claim 13 wherein said blending comprises blending into a polymer resin the bisaryl diphosphate product that is obtained by a process that includes:
   (a) reacting bisphenol A with a catalyst/phosphorus oxyhalide mixture to produce a diphosphorotetrahalide intermediate, wherein said bisphenol A contains less than about 200 ppm water; and
   (b) reacting said diphosphorotetrahalide intermediate with phenol to form bisphenol A bis(diphenyl)phosphate.

15. The method of claim 9 wherein said bisaryl diphosphate is prepared by a process that includes:
   (a) reacting a dihydric aromatic compound with a catalyst/phosphorus oxyhalide mixture to produce a diphosphorotetrahalide intermediate; and
   (b) reacting said diphosphorotetrahalide intermediate with an alcohol to form the desired bisaryl diphosphate, wherein said alcohol contains less than about 300 ppm water.

16. The method of claim 15 wherein the method comprises adding to a polymer resin the bisaryl diphosphate product that is obtained by a process that includes:
   (a) reacting bisphenol A with a catalyst/phosphorus oxyhalide mixture to produce a diphosphorotetrahalide intermediate; and
   (b) reacting said diphosphorotetrahalide intermediate with phenol to form bisphenol A bis(diphenyl)phosphate, wherein said phenol contains less than about 300 ppm water.

* * * * *